United States Patent [19]

Popelka

[11] 4,195,932

[45] Apr. 1, 1980

[54] ABSORPTION SPECTROPHOTOMETER

[75] Inventor: Susan R. Popelka, Gurnee, Ill.

[73] Assignee: Abbott Laboratories, North Chicago, Ill.

[21] Appl. No.: 921,304

[22] Filed: Jul. 3, 1978

[51] Int. Cl.² ............................................. G01N 21/02
[52] U.S. Cl. ................................ 356/407; 356/414; 356/419
[58] Field of Search ............... 356/320, 407, 410, 411, 356/414, 419, 425

[56] References Cited

U.S. PATENT DOCUMENTS

| | | | |
|---|---|---|---|
| 3,770,354 | 11/1973 | Tsoruta et al. | 356/407 |
| 3,941,487 | 3/1976 | Ehret et al. | 356/411 |
| 4,120,591 | 10/1978 | van Valkenborg | 356/407 |

Primary Examiner—Vincent P. McGraw

[57] ABSTRACT

The present invention encompasses an absorption spectrophotometer comprising:
a light source for irradiating a test sample; a means for focusing light from the light source to a location within the test sample; and a means for concentrating light transmitted through the test sample onto a beam splitting element which separates the light received into a test beam and a reference beam and directs the test beam through a first interference filter which passes light corresponding to an absorption band of the test sample to a first detector, and directs the reference beam through a second interference filter which passes a band of light outside the absorption band of the test sample to a second detector.

2 Claims, 2 Drawing Figures

ABSORPTION SPECTROPHOTOMETER

BACKGROUND OF THE INVENTION

A variety of absorption spectrophotometers are known; *Instrumental Methods of Analysis*, 3rd Edition, 1958; Willard, Merrill and Dean P. Van Nostrand Company, Inc., Princeton, N.J., pages 96–138. These devices are characterized as having a source of radiant energy, a monochromator, that is a device for isolating narrow bands of radiant energy from the source, cells or holders for the substances under investigation, and a device to receive and detect radiant energy. Generally, a blank sample is inserted and the light passing is considered 100% transmittance or optical density of zero. Percent transmittance for an unknown is compared to percent transmittance for a set of standards of known concentration to determine the concentration of the unknown. Optical density is related to concentration as follows:

$$\text{Optical Density} = \log(I_O = Elc/I)$$

E = extinction coefficient in liter/mole/cm.
l = length of cell in cm
c = concentration moles per liter
$I_O$ = incident light into the sample
I = exit light from the sample
and % transmittance = $I/I_O \times 100$

DETAILED DESCRIPTION OF THE INVENTION

Figure 1:
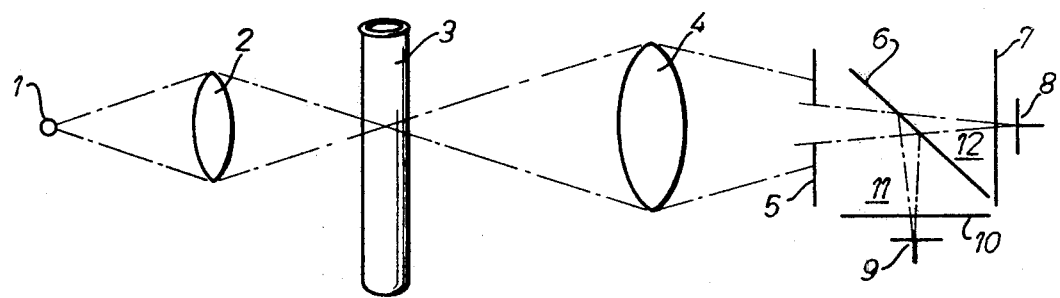
FIG. 1, schematic view of the absorption spectrophotometer.
Figure 2:
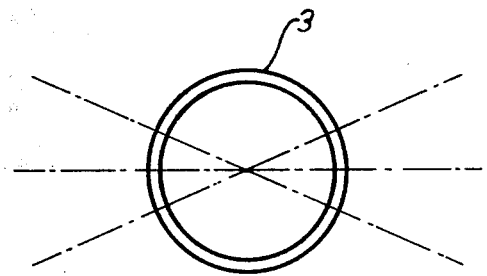
FIG. 2, is a cross-sectional view of light focused at a location within the test sample.

The present invention is an absorption spectrophotometer comprising:

a light source for irradiating a test sample, a means for focusing light from the light source to a location within the test sample; and a means for concentrating light transmitted through the test sample onto a beam splitting element which separates the light received into a test beam and a reference beam and directs the test beam to a first interference filter which passes light corresponding to an absorption band of the test sample to a first detector, and directs the reference beam to a second interference filter which passes a band of light outside the absorption band of the test sample to a second detector.

A preferred absorption spectrophotometer according to the present invention comprising:

(a) a light source for irradiating a test sample;
(b) a first lens located between the light source and test sample, positioned for focusing light to a location within the test sample;
(c) a second lens positioned for receiving light transmitted through the test sample, said second lens concentrating light received from the test sample; and
(d) a dichroic filter positioned for receiving light from the second lens, said dichroic filter separating light from the second lens into a test beam and a reference beam directing the test beam to a first interference filter which passes light corresponding to an absorption band of the test sample to a first detector, and directing the reference beam to a second interference filter which passes a band of light outside the absorption band of the test sample to a second detector.

A light shielding element having an aperture is advantageously placed between the second lens and the beam splitting element to reduce the light available to the detectors and thereby prevent saturation.

A tungsten lamp is a suitable source of light. Other sources of white light are conveniently adapted as a light source.

A biconvex lens located between the light source and the test sample is a preferred means for focusing light to a location within the test sample. Focusing light to a location within the test sample is an important feature of the present invention in that errors due to test tube deviations are greatly reduced. Concave mirrors are also suitable means for focusing light to a location within the test sample.

A round test tube mounted by a frictional collar in a light receiving relationship with respect to the means for focusing light so that light is focused at a location within the test sample is a preferred sample cell.

A biconvex lens is a preferred means for concentrating light transmitted through the test sample onto a beam splitting element. Thus, diverging light from the test sample is concentrated on the beam splitting element. It is preferred that the light concentrating means focus light on the detector. Concave mirrors are alternate means for concentrating light.

The beam splitting element serves to separate light which has passed through the sample into a test beam and a reference beam.

The beam splitting element may simply divide the light beam into two full spectrum beams: a test beam which is then filtered to pass light of a wavelength absorbed by the test sample to a light detector and a reference beam which is then filtered to pass light of a wavelength not absorbed by the test sample to a light detector. This type of beam splitting is accomplished by a plate-type, cube-type or pellicle-type beam splitting element.

The plate-type beam splitting elements are crown glass plates coated with a partial reflecting dielectric material on the face receiving light and non-reflecting material on the remote side. These devices are mounted at a 45° angle with respect to an incident beam of light. A portion of the incident beam is transmitted and a portion is reflected perpendicular to the incident beam.

A cube splitting element consists of pairs of identical right-angle prisms, with hypotenuse faces cemented together. Prior to cementing a metal dielectric film is often vacuum-deposited on one of the hypotenuse faces. The cubic beam splitting element is aligned so that light strikes the hypotenuse face at a 45° angle. A portion of the light continues uninterrupted and a portion is diverted at 90° to the incident beam.

Pellicle beam splitting elements are made of high tensile strength elastic membranes about 7 micrometers thick. When mounted so that the angle of incidence is 45° like the other beam splitting devices, a portion of the light is transmitted substantially uninterrupted and a portion is reflected 90° to the incident beam.

A dichroic filter is a preferred beam splitting element. These devices are commonly used for color matching in the color printing and color television industries. Dichroic filters are made of alternating layers of high and low index dielectric material in quarter wavelength layers so that light rays of certain wavelengths are reflected and other wavelengths are transmitted substantially, uninterrupted. These devices separate by wavelengths. In this embodiment, the test beam contains light of the wavelength absorbed by the test sample and, therefore, will vary in intensity depending on the concentration of substance analysed. The reference beam will contain light of a wavelength not absorbed by the test sample and will remain nearly constant and serve as an internal light standard, a reference beam. Dichroic filters are preferred because of their efficiency in transmitting and reflecting light.

The interference filters merely pass narrower bands of light to the detectors. In the case of the test beam, a band of light centered about the peak absorption in the test sample is transmitted to the light detector. In the case of the reference beam, a narrow band of light of wavelength well outside of the absorption of the test sample is transmitted to a light detector. The light path length from the light source to each detector is preferably the same.

Detectors are common light monitoring means such as photomultiplier tubes and solid-state silicon detectors.

Now referring to FIG. 1, a tungsten halogen lamp 1 emits white light, a portion of which is focused to a location within the test sample 3 by a biconvex lens 2. Light transmitted through the test sample in a test tube 3 is concentrated by a biconvex lens 4 on a dichroic beam splitting element 6. Lens 4 focuses light on the solid-state silicon light detectors 8 and 9. The dichroic 6 splits the incident beam into a reference beam 12 which passes through an interference filter 7 to detector 8 and a test beam 11 which pases through interference filter 10 to detector 9. In operation, blank and standard samples are introduced by placing and removing test tubes containing samples into a test tube holder or port and voltage outputs at the detectors 8 and 9 are measured by conventional voltage measuring means.

5 is a light shielding element having an aperture which controls the amount of light falling on the detectors. Specifications for elements of a preferred embodiment are as follows: Tungsten Halogen Lamp: (Color Temperature, 3100° K.; Watts, 12 W; Volts, 12 V; Filament Size, 2.3 mm length, 0.8 mm width). First Biconvex Lens: (Focal Length, 15 mm; Back Focal Length, 12.9 mm; Center Thickness, 5.9 mm; Edge Thickness, 2.0 mm; Diameter, 14.5 mm; Index of Refraction, 1.523). Sample Holder: (12×75 mm, Round Test Tube; Light Beam Enters Sample at 17.8 mm Above the Bottom of the Test Tube). Second Biconvex Lens: (Focal Length, 25.4 mm; Back Focal Length, 24.2 mm; Center Thickness, 3.6 mm; Edge Thickness, 2.0 mm; Diameter, 12.7 mm; Index of Refraction, 1.523). Light Shield: (having an aperture of 3.0 mm diameter) Dichroic: (Reflection at 492 nm: >99%, Transmission at 600 nm, 22%; Reflection at wavelengths longer than 600 nm: >20%; Dimensions, 0.75"×0.75"×0.125" thick). 492 nm Interference Filter: (Center Wavelength, 492 nm; Half Power Bandwidth, 10 nm; Blocking, $10^{-4}$ from 200 nm to 2000 nm; Transmission, 50–65% at peak wavelength; Dimensions, 0.75"×0.75"×0.125" thick). 600 nm Interference Filter: (Center Wavelength, 600 nm; Half Power Bandwidth, 10 nm; Blocking, $10^{-4}$ from 200 nm to 2000 nm; Transmission, 50–65% at peak wavelength; Dimensions, 0.75"×0.75"×0.125" thick). Test Wavelength Detector: (492 nm, solid state silicon light detector having 0.20 amps/watt responsivity at 490 nm and active area of 5 mm diameter). Reference Wavelength Detector: (600 nm, solid state silicon light detector having 0.30 amps/watts responsivity at 600 nm and active area of 5 mm diameter).

The tungsten lamp is mounted 27.9 mm from the first biconvex lens. The center of the test sample is 27.9 mm on the other side of the first biconvex lens and positioned so that light from this lens focuses in the center of the test tube. The distance from the center of the test tube to the second biconvex lens is 49.6 mm and the distance from the second convex lens to the center of the dichroic beam splitting element is 29.2 mm. The dichroic beam splitting element receives light at a 45° angle. The 600 nm interference filter is 9 mm beyond the dichroic, and the reference detector is 11.4 mm beyond that. The 492 nm interference receives reflected light 9 mm below the dichroic and the test detector lies 11.4 mm beyond that.

A light shield having an aperture of 3.0 mm is located 3.7 mm in front of the second biconvex lens and 25.5 nm in front of the dichroic. The aperture is a 3.0 mm diameter tunnel which limits light so as to prevent saturation of the detectors. The size of the aperture varies with the characteristic of the detectors.

Oxidation of orthophenylenediamine, a common analytical reagent, results in an absorption in a test sample at 492 nm, which can be conveniently monitored by the absorption spectrophotometer of the present invention using a reference band above 550 nm, preferably 600 nm.

The dichroic, first and second interference filter are conveniently arranged in a cubic modular unit. The dichroic is mounted on the diagonal of the cube, an aperture in one wall permits light from the second lens to strike the dichroic. The first interference filter is mounted in the wall of the module opposite the aperture to receive light passing through the dichroic. The second interference filter is mounted in a wall of the module to receive light reflected at 90° by the dichroic.

The foregoing embodiments are intended to illustrate the present invention and not to limit it in spirit or scope.

What is claimed is:

1. An absorption spectrophotometer comprising:
   (a) a light source for irradiating a test sample;
   (b) a first lens located between the light source and test sample, positioned for focusing light to a location within the test sample;
   (c) a second lens positioned for receiving light transmitted through the test sample, said second lens concentrating light received from the test sample;
   (d) a dichroic filter positioned for receiving light from the second lens, said dichroic filter separating light from the second lens into a test beam and a reference beam, directing the test beam to a first interference filter which passes light corresponding to an absorption band of the test sample to a first detector, and directing the reference beam to a second interference filter which passes a band of light outside the absorption band of the test sample to a second detector, said first and second detectors located equal distances from the dichroic filter said second lens focusing light on the first and second detectors; and
   (e) a light shielding element defining an aperture for passage of light from the second lens to the dichroic filter, said light shielding element limiting the amount of light passing to the dichroic filter and thereby preventing saturation of the first and second detectors.

2. An absorption spectrophotometer, according to claim 1, wherein the light shielding element defining an aperture, dichroic filter and first and second interference filters are constructed in a modular unit.

* * * * *